(12) United States Patent
Pappone et al.

(10) Patent No.: US 11,596,470 B2
(45) Date of Patent: *Mar. 7, 2023

(54) IRRIGATED CATHETER

(71) Applicant: ST. JUDE MEDICAL, ATRIAL FIBRILLATION DIVISION, INC., St. Paul, MN (US)

(72) Inventors: Carlo Pappone, Lecco (IT); Alan de la Rama, Cerritos, CA (US); Peter Chen, Irvine, CA (US); Cary Hata, Irvine, CA (US)

(73) Assignee: ST. JUDE MEDICAL, ATRIAL FIBRILLATION DIVISION, INC., St. Paul, MN (US)

( * ) Notice: Subject to any disclaimer, the term of this patent is extended or adjusted under 35 U.S.C. 154(b) by 705 days.

This patent is subject to a terminal disclaimer.

(21) Appl. No.: 16/543,277

(22) Filed: Aug. 16, 2019

(65) Prior Publication Data

US 2020/0038103 A1 Feb. 6, 2020

Related U.S. Application Data

(63) Continuation of application No. 14/288,017, filed on May 27, 2014, now Pat. No. 10,433,903, which is a
(Continued)

(51) Int. Cl.
*A61B 18/14* (2006.01)
*A61M 25/00* (2006.01)
(Continued)

(52) U.S. Cl.
CPC ....... *A61B 18/1492* (2013.01); *A61M 25/003* (2013.01); *A61M 25/0071* (2013.01);
(Continued)

(58) Field of Classification Search
CPC ........ A61B 18/1492; A61B 2018/1467; A61B 2018/1497; A61M 25/003; A61M 25/0071
See application file for complete search history.

(56) References Cited

U.S. PATENT DOCUMENTS

| 4,325,374 A | 4/1982 | Komiya |
| 5,163,905 A | 11/1992 | Don Michael |

(Continued)

FOREIGN PATENT DOCUMENTS

| EP | 109178 B1 | 5/1992 |
| JP | 2006509547 A | 3/2006 |

(Continued)

OTHER PUBLICATIONS

"International Search Report and Written Opinion of the International Searching Authority", PCT/US2010/049836 dated Nov. 15, 2010.

*Primary Examiner* — Michael F Peffley
*Assistant Examiner* — Samantha M Good
(74) *Attorney, Agent, or Firm* — Armstrong Teasdale LLP

(57) ABSTRACT

A fluid delivery catheter configured to allow optimal fluid distribution through each electrode by varying the diameter of a catheter lumen is disclosed. Uniform or different fluid flow rates through longitudinally spaced apart elution holes may be achieved. Exemplary fluids for use with the catheter include a cooling fluid, a therapeutic fluid, and a medication.

20 Claims, 8 Drawing Sheets

Related U.S. Application Data continuation of application No. 11/696,646, filed on Apr. 4, 2007, now Pat. No. 8,764,742.

(51) Int. Cl.
  *A61M 25/10* (2013.01)
  *A61B 18/00* (2006.01)

(52) U.S. Cl.
  CPC .... *A61M 25/1002* (2013.01); *A61M 25/1011* (2013.01); *A61B 2018/00029* (2013.01); *A61B 2018/1467* (2013.01); *A61B 2018/1497* (2013.01); *A61B 2218/002* (2013.01); *A61M 25/007* (2013.01); *A61M 2025/0034* (2013.01); *A61M 2025/1093* (2013.01)

(56) References Cited

U.S. PATENT DOCUMENTS

| | | | |
|---|---|---|---|
| 5,279,299 A | 1/1994 | Imran | |
| 5,364,352 A | 11/1994 | Cimino et al. | |
| 5,378,230 A | 1/1995 | Mahurkar | |
| 5,462,521 A | 10/1995 | Brucker et al. | |
| 5,487,385 A | 1/1996 | Avitall | |
| 5,520,682 A | 5/1996 | Baust et al. | |
| 5,545,200 A | 8/1996 | West et al. | |
| 5,569,220 A | 10/1996 | Webster, Jr. | |
| 5,681,280 A | 10/1997 | Rusk et al. | |
| 5,772,642 A | 6/1998 | Ciamacco, Jr. et al. | |
| 5,792,140 A | 8/1998 | Tu et al. | |
| 5,800,428 A | 9/1998 | Nelson et al. | |
| 5,833,632 A | 11/1998 | Jacobsen et al. | |
| 5,853,425 A | 12/1998 | Houser | |
| 5,893,885 A | 4/1999 | Webster, Jr. | |
| 5,902,328 A | 5/1999 | LaFontaine et al. | |
| 5,919,188 A | 7/1999 | Shearon et al. | |
| 5,944,022 A | 8/1999 | Nardella et al. | |
| 5,951,471 A | 9/1999 | De La Rama et al. | |
| 5,954,719 A | 9/1999 | Chen et al. | |
| 5,992,418 A | 11/1999 | De La Rama et al. | |
| 6,001,095 A | 12/1999 | De La Rama et al. | |
| 6,010,500 A | 1/2000 | Sherman et al. | |
| 6,017,338 A | 1/2000 | Brucker et al. | |
| 6,030,382 A | 2/2000 | Fleischman et al. | |
| 6,053,912 A | 4/2000 | Panescu et al. | |
| 6,063,080 A | 5/2000 | Nelson et al. | |
| 6,080,151 A | 6/2000 | Swartz et al. | |
| 6,171,275 B1 | 1/2001 | Webster, Jr. | |
| 6,210,409 B1 | 4/2001 | Ellman et al. | |
| 6,217,573 B1 | 4/2001 | Webster | |
| 6,233,476 B1 | 5/2001 | Strommer et al. | |
| 6,235,022 B1 | 5/2001 | Hallock et al. | |
| 6,251,134 B1 | 6/2001 | Alt et al. | |
| 6,273,876 B1 | 8/2001 | Klima et al. | |
| 6,325,797 B1 | 12/2001 | Stewart et al. | |
| 6,346,104 B2 | 2/2002 | Daly et al. | |
| 6,356,790 B1 | 3/2002 | Maguire et al. | |
| 6,379,349 B1 | 4/2002 | Mueller et al. | |
| 6,385,472 B1 | 5/2002 | Hall et al. | |
| 6,405,067 B1 | 6/2002 | Mest et al. | |
| 6,463,632 B2 | 10/2002 | Craig et al. | |
| 6,464,632 B1 | 10/2002 | Taylor | |
| 6,493,590 B1 | 12/2002 | Wessman et al. | |
| 6,498,944 B1 | 12/2002 | Ben-Haim et al. | |
| 6,522,930 B1 | 2/2003 | Schaer et al. | |
| 6,604,003 B2 | 8/2003 | Fredricks et al. | |
| 6,611,699 B2 | 8/2003 | Messing | |
| 6,780,183 B2 | 8/2004 | Jimenez et al. | |
| 6,796,966 B2 | 9/2004 | Thomas | |
| 6,921,397 B2 | 7/2005 | Corcoran et al. | |
| 6,980,843 B2 | 12/2005 | Eng et al. | |
| 7,013,169 B2 | 3/2006 | Bowe | |
| 7,137,395 B2 | 11/2006 | Fried et al. | |
| 7,197,354 B2 | 3/2007 | Sobe | |
| 7,263,397 B2 | 8/2007 | Hauck et al. | |
| 7,389,148 B1 | 6/2008 | Morgan | |
| 7,416,552 B2 | 8/2008 | Paul et al. | |
| 7,468,027 B2 | 12/2008 | Barbut et al. | |
| 7,536,218 B2 | 5/2009 | Govari et al. | |
| 7,537,596 B2 | 5/2009 | Jensen | |
| 7,565,208 B2 | 7/2009 | Harris et al. | |
| 7,615,050 B2 | 11/2009 | Cross et al. | |
| 7,669,309 B2 | 3/2010 | Johnson et al. | |
| 7,699,771 B2 | 4/2010 | Wendlandt et al. | |
| 7,706,891 B2 | 4/2010 | Hastings et al. | |
| 7,824,406 B2 | 11/2010 | Wang et al. | |
| 7,824,517 B2 | 11/2010 | Kampa et al. | |
| 7,857,810 B2 | 12/2010 | Wang et al. | |
| 7,873,401 B2 | 1/2011 | Shachar | |
| 8,517,999 B2 | 8/2013 | Pappone et al. | |
| 8,764,742 B2 | 7/2014 | Pappone et al. | |
| 10,433,903 B2 * | 10/2019 | Pappone | A61M 25/1002 |
| 2001/0012956 A1 | 8/2001 | Behl et al. | |
| 2002/0058866 A1 | 5/2002 | Segner et al. | |
| 2002/0072710 A1 | 6/2002 | Stewart et al. | |
| 2002/0156420 A1 | 10/2002 | Anderson et al. | |
| 2003/0125730 A1 | 7/2003 | Berube et al. | |
| 2004/0015215 A1 | 1/2004 | Fredricks et al. | |
| 2004/0034348 A1 | 2/2004 | Rashidi | |
| 2004/0064158 A1 | 4/2004 | Klein et al. | |
| 2004/0143256 A1 | 7/2004 | Bednarek | |
| 2004/0153056 A1 | 8/2004 | Muller et al. | |
| 2004/0181138 A1 | 9/2004 | Hindricks et al. | |
| 2004/0204671 A1 | 10/2004 | Stubbs et al. | |
| 2004/0220461 A1 | 11/2004 | Schwartz | |
| 2004/0236350 A1 | 11/2004 | Lewis et al. | |
| 2004/0267106 A1 | 12/2004 | Segner et al. | |
| 2005/0004563 A1 | 1/2005 | Racz et al. | |
| 2005/0043713 A1 | 2/2005 | Zhou | |
| 2005/0049583 A1 | 3/2005 | Swanson | |
| 2005/0054989 A1 | 3/2005 | McGuckin et al. | |
| 2005/0070894 A1 | 3/2005 | McClurken | |
| 2005/0096647 A1 | 5/2005 | Steinke et al. | |
| 2005/0143729 A1 | 6/2005 | Francischelli et al. | |
| 2005/0187561 A1 | 8/2005 | Lee-Sepsick et al. | |
| 2005/0197633 A1 | 9/2005 | Schwartz et al. | |
| 2005/0204671 A1 | 9/2005 | Heuvel et al. | |
| 2005/0272975 A1 | 12/2005 | McWeeney et al. | |
| 2006/0004353 A1 | 1/2006 | Koyfman et al. | |
| 2006/0009740 A1 | 1/2006 | Higgins et al. | |
| 2006/0015126 A1 | 1/2006 | Sher | |
| 2006/0064123 A1 | 3/2006 | Bonnette et al. | |
| 2006/0149192 A1 | 7/2006 | Deniega et al. | |
| 2006/0200191 A1 | 9/2006 | Zadno-Azizi | |
| 2006/0265043 A1 | 11/2006 | Mandrusov et al. | |
| 2006/0287650 A1 | 12/2006 | Cao et al. | |
| 2007/0005053 A1 | 1/2007 | Dando | |
| 2007/0021743 A1 | 1/2007 | Rioux et al. | |
| 2007/0060847 A1 | 3/2007 | Leo et al. | |
| 2007/0156114 A1 | 7/2007 | Worley et al. | |
| 2007/0179491 A1 | 8/2007 | Kratoska et al. | |
| 2007/0299424 A1 | 12/2007 | Cumming et al. | |
| 2008/0091193 A1 | 4/2008 | Kauphusman et al. | |
| 2008/0091195 A1 | 4/2008 | Sliwa et al. | |
| 2008/0139999 A1 | 6/2008 | Gibson et al. | |
| 2008/0161788 A1 | 7/2008 | Dando et al. | |
| 2008/0161789 A1 | 7/2008 | Thao et al. | |
| 2008/0275428 A1 | 11/2008 | Tegg et al. | |
| 2008/0281319 A1 | 11/2008 | Paul et al. | |
| 2008/0294158 A1 | 11/2008 | Pappone et al. | |
| 2008/0312713 A1 | 12/2008 | Wilfley et al. | |
| 2009/0012517 A1 | 1/2009 | De La Rama et al. | |
| 2009/0018497 A1 | 1/2009 | Birchard et al. | |
| 2009/0228092 A1 | 9/2009 | Raeder-Devens et al. | |
| 2009/0247993 A1 | 10/2009 | Kirschenman et al. | |
| 2009/0287210 A1 | 11/2009 | Kauphusman et al. | |
| 2010/0004632 A1 | 1/2010 | Wu et al. | |
| 2010/0174177 A1 | 7/2010 | Wu | |

FOREIGN PATENT DOCUMENTS

| | | |
|---|---|---|
| JP | 2002513652 A5 | 6/2006 |
| JP | 2008136875 A | 6/2008 |
| JP | 2008541799 A5 | 5/2009 |

(56) References Cited

FOREIGN PATENT DOCUMENTS

| | | |
|---|---|---|
| JP | 03162588 U | 9/2010 |
| JP | 2010533564 A5 | 8/2011 |
| WO | 2005048858 A1 | 6/2005 |
| WO | 2005094661 A1 | 10/2005 |
| WO | 2007015139 A2 | 2/2007 |
| WO | 2007035554 A1 | 3/2007 |
| WO | 2008010039 A2 | 1/2008 |

* cited by examiner

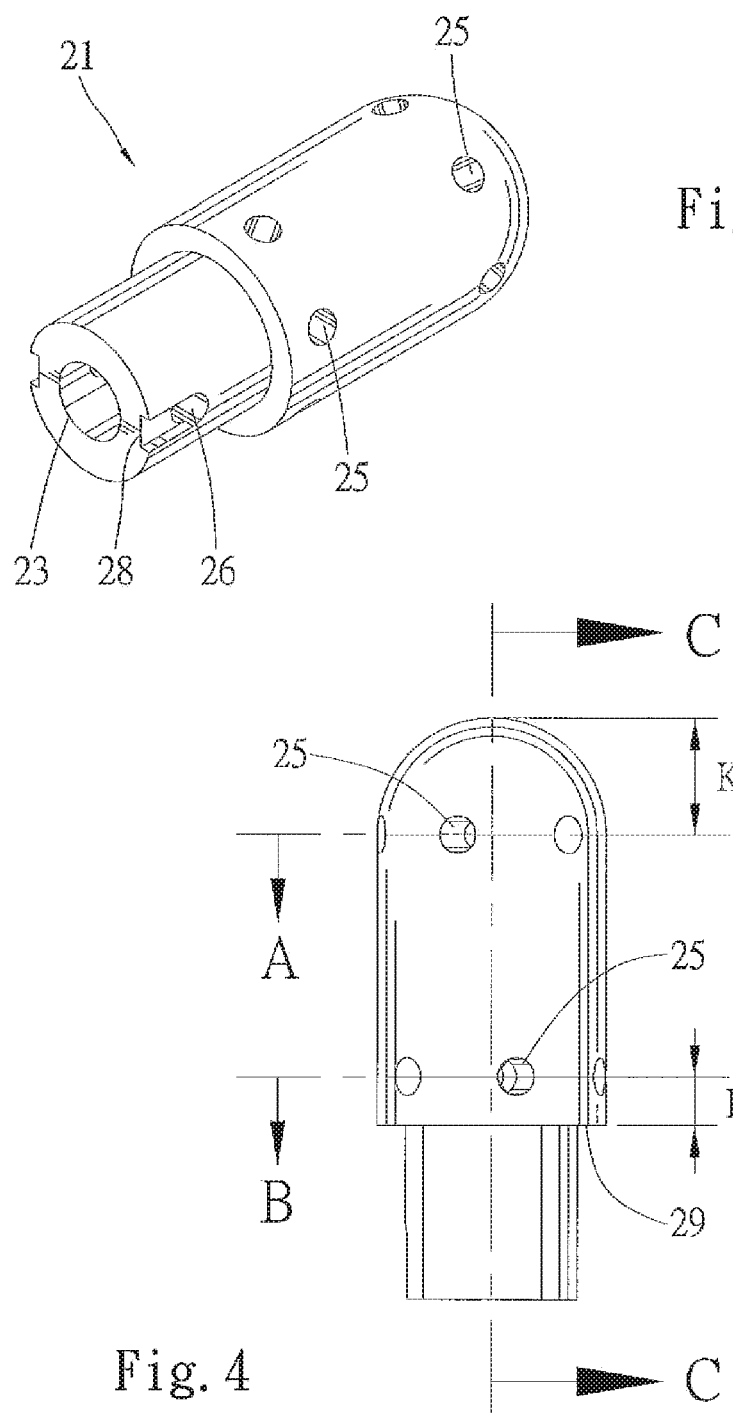

IRRIGATED CATHETER

CROSS-REFERENCE TO RELATED APPLICATIONS

This patent application is a Continuation of U.S. patent application Ser. No. 14/288,017 filed May 27, 2014, issued as U.S. Pat. No. 10,433,903, which is a Continuation of U.S. patent application Ser. No. 11/696,646 filed Apr. 4, 2007, issued as U.S. Pat. No. 8,764,742. The '017 application and the '742 patent are hereby incorporated by reference as though fully set forth herein.

FIELD OF THE INVENTION

The field of the invention is catheters.

BACKGROUND OF THE INVENTION

Ablation catheters using RF (radio frequency) energy are known. A typical ablation catheter has electrodes located at the catheter tip and delivers RF energy to ablate selected tissue areas in a patient. For example, patients with arrhythmia experience irregular heart beats caused by arrhythmogenic electrical signals generated in cardiac tissues. Such patients may be treated by ablating those cardiac tissues that generate such unintended electrical signals with RE energy. With the help of sensing and mapping tools, an electrophysiologist can determine the region of cardiac tissue targeted for ablation. Once determined, a catheter tip having one or more electrodes is positioned over the targeted tissue. Then, the user sends RF energy from the generator to the electrodes, creating sufficient heat to damage the targeted tissue. By damaging and scarring the targeted tissue, aberrant electrical signal generation or transmission is interrupted.

Application of curative energy is currently performed endocardially with the objective of reaching the epicardium to create a fully transmural. This is important in all arrhythmias especially during ablation for atrial fibrillation and ventricular tachycardia. In the former case, transmural lesions are required to create conduction block to isolate relevant structures while in the latter case the arrhythmogenic substrate is located often in the epicardial layer of ventricular walls. Delivery of the energy is limited by the increase of temperature at the interface between catheter tip and endocardial surface and there is a good correlation between thrombus formation and high temperature. A temperature sensor is typically provided near the tip of the catheter so the user may monitor the operating temperature to ensure that overheating does not occur in the catheter tip and in the surrounding tissues. One known solution to prevent overheating is by having an irrigation system embedded within the catheter. In brief; a typical irrigation system includes a delivery lumen inside of the catheter body to supply cooling fluid, such a saline, from a pump to the catheter tip. An irrigation system may internally irrigate the catheter tip, where the cooling fluid circulates within the catheter tip. Another type of irrigation system delivers cooling fluid from within the catheter tip to the outside of the catheter tip which also cools the surrounding tissues. Catheters with an irrigated tip allow the delivery of more energy with a lower temperature at the tissue/catheter interface thus minimizing thrombus formation while maximizing deep lesion creation in the tissue. Despite numerous desirable properties, however, known irrigated catheters have several disadvantages. For example, because the temperature of the catheter tip region can vary depending on factors such as its proximity to an electrode and irrigation duct, it is difficult to monitor and ensure that all heated surfaces along the catheter tip are adequately cooled. Often the catheter tip is positioned not perpendicularly to the tissue but tangentially to increase the tip/tissue contact area as for example during ablation of the inferior part of the right sided pulmonary vein. In this situation and in every other situation where a tip side/tissue contact is required, a uniform cooling of the catheter tip would further reduce thrombus formation while allowing development of larger electrodes to more efficiently deliver energy for ablation. In this way the entire electrode surface can be used to ablate a pathological tissue without overheating any portion of the catheter tip and causing thrombus formation.

The coronary sinus (CS) is increasingly recognized as one of the major structures contributing in many types of supraventricular tachycardias including atrial fibrillation. In this case many anatomical and electrophysiological features can promote atrial fibrillation maintenance, especially in patients with a long-standing arrhythmia. As a matter of fact, the CS connects anatomically and electrophysiologically the right atrium and the left atrium with special characteristics of slow and anisotropic conduction, allowing micro- and macro-reentry during organized and unorganized atrial fibrillation. On the right atrial side, broad and thick muscular connections can be observed at the CS ostium, while different anatomic studies have demonstrated the existence of discrete and multiple connections (average 5±2) between the CS body and the LA postero-inferior and postero-lateral walls. This muscular extension of the left atrial wall into the CS shows marked anisotropy, and mapping their insertion with conventional bipolar and quadripolar catheters is relatively difficult given also the oblique insertion of these sleeves across the posterior pericardial space.

The role of the CS is increasingly recognized in maintaining persistent and permanent atrial fibrillation which constitute up to 70% of the atrial fibrillation cases in the population referred for catheter ablation. On one side during ablation of long-standing atrial fibrillation, disconnection of the coronary sinus from both the let and right atrium can be required in up to 60% of cases to interrupt the arrhythmia or to organize the electrical activity in a discrete mappable atrial tachycardia. On the other side, mitral isthmus ablation to create a bi-directional line of block is increasingly performed to organize the substrate during chronic atrial fibrillation ablation. To create a bi-directional block, ablation within the CS has to be performed in 30-50% of cases. The role of CS as a critical part of left atrial tachycardia is also increasingly known. Effective mitral isthmus block in the settings of perimitral atrial flutter can require ablation in the CS in up to 50% of cases to interrupt the arrhythmia and make it no longer inducible. The CS is also important in the ablation of postero-septal and left-sided accessory pathways, as in man y cases the ventricular and/or atrial insertion of the accessory pathway is too epicardial for endocardial ablation using a conventional catheter. Furthermore mapping the CS body with a conventional multi-polar catheter is not quite efficient since this type of catheter is not able to deliver radiofrequency energy.

Thus, there remains a need for a balloon or a mesh expandable catheter that could be inserted deeply inside the CS, inflated and then slowly pulled back towards the CS ostium while delivering equatorially curative energy source such as radiofrequency or therapeutic ultrasound to fully disconnect the CS musculature from the left and right atrium in atrial fibrillation, atrial tachycardia or WPW ablation. It would be more beneficial clinically if this balloon catheter consists of multiple ablating irrigated electrodes where the irrigation pattern is controlled to provide desired relative uniform cooling to the ablating electrodes to minimize coagulum formation and create larger and longer lesions safely.

SUMMARY OF THE INVENTION

Embodiments of catheters, systems and methods are disclosed that, provide, among other things, substantially uniform cooling of ablation electrodes and/or the surrounding tissues in use. The catheter may include an elongated tubular catheter body having a distal end, a proximal end, and a lumen extending longitudinally within the catheter body. A number of elution holes may be provided in each electrode, and these holes are in fluid communication with the lumen through ducts. As such, a cooling fluid may be delivered from a pump, through the lumen, through the ducts, and out of the holes to the environment outside of the catheter.

Contemplated catheters may have at least one electrode positioned at the distal end, and the lumen may have varying diameters throughout so as to provide a desired fluid outflow pattern when flowing out of elution holes. Of the many contemplated patterns, it is desired that the varying lumen diameters is configured such that fluid outflow rate at all of the elution holes is substantially the same. Among the many different possibilities contemplated, the lumen may have a diameter that is smaller at a distal end than at a proximal end. Further, it is contemplated that the decrease in diameter may be defined by a tapered section in the lumen.

The ducts may be positioned at a tilted angle from the main lumen, or can be substantially perpendicular to the main lumen. In exemplary embodiments the ducts and the main lumen are formed at angles between 35 to 90 degrees, more specifically, 45 to 90 degrees, even more specifically between 80 to 90 degree angles, and even substantially 90 degrees. In embodiments where the ducts are tilted, they can tilt forward and also backward.

Contemplated lumen diameters may vary from about 0.005 inches to about 0.045 inches, and the tapered section may decrease the diameter by about 5% to about 40%.— when comparing the two diameters immediately adjacent the tapered section. In other embodiments, there are no such tapered sections, and the diameter gradually decreases along the distal region of the catheter.

In some embodiments of the contemplated device, the catheter may have at least six ducts at a single junction with the main lumen, and these ducts may be evenly and radially spread out, evenly angled from each other to form a complete circle of 360 degrees.

The ducts optionally have an inner surface with a surface pattern that causes the outflow of cooling fluid to form an irregular pattern upon exiting the holes. For example, the pattern is a spiral groove, so that the spraying pattern is an outwardly spraying swirl.

The catheter may also include at least one inflatable balloon. In some embodiments, the balloon may be attached to less than 60% of a circumference of a section of the catheter body, instead of completely surrounding a longitudinal section of the catheter body; or in another embodiment, the balloon may be attached to less than 52% of a circumference of a section of the catheter body.

The optional balloons can have an inflated shape such as a half-dome. Other suitable shapes can also be implemented depending on the shape and size of the body lumen and tissue area intended for treatment.

Further, the balloons can be positioned opposite to elution holes and/or electrodes so that the inflatable balloon can assist in physically pressing the electrodes to the targeted tissue for ablation.

BRIEF DESCRIPTION OF THE DRAWING

FIG. 3 is a perspective view of the catheter tip according to an aspect of the inventive subject matter.

FIG. 4 is a side view of the catheter tip according to an aspect of the inventive subject matter.

DETAILED DESCRIPTION

The invention can now be better understood by turning to the following detailed description of numerous embodiments, which are presented as illustrated examples of the invention defined in the claims. It is expressly understood that the invention as defined by the claims may be broader than the illustrated embodiments described below.

Many alterations and modifications may be made by those having ordinary skill in the art without departing from the spirit and scope of the invention. Therefore, it must be understood that the illustrated embodiment has been set forth only for the purposes of example and that it should not be taken as limiting the invention as defined by the following claims. For example, notwithstanding the fact that the elements of a claim are set forth below in a certain combination, it must be expressly understood that the invention includes other combinations of fewer, more or different elements, which are disclosed herein even when not initially claimed in such combinations.

As used herein, the term "duct" is synonymous with "side channel", both are used herein to describe fluid delivery paths branching off of the main lumen of the catheter.

Figure 1:
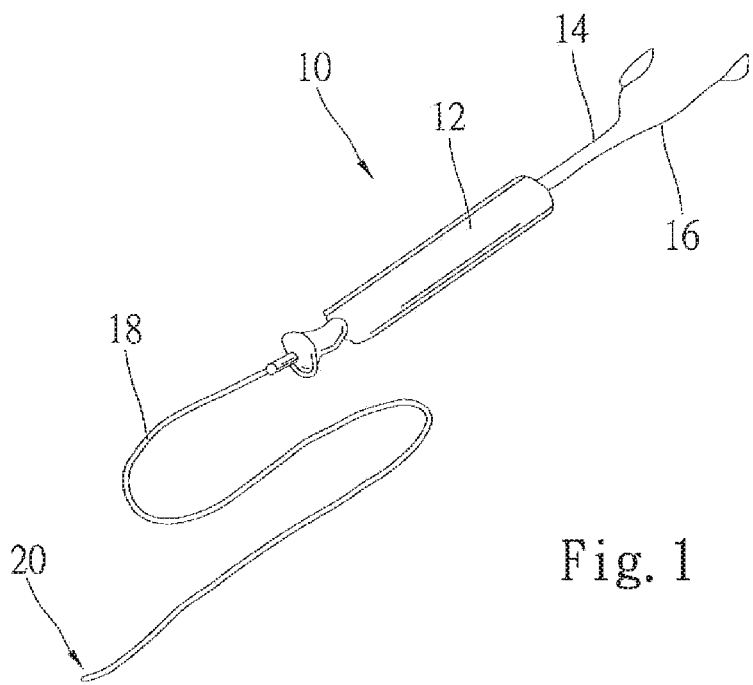
FIG. 1 is a perspective view of an irrigation catheter system according to an aspect of the inventive subject matter.

Referring now to FIG. 1, which illustrates a catheter system 10, having a control unit body 12, tubing sets 14 and 16, and an elongated catheter body 18 with a distal region 20. Tubing sets 14 and 16 can be connected to any suitable known devices in the art such as, for example, a monitor/display, RF generator, signal processor, fluid pump, etc. The system 10 may also use a temperature sensor and mapping tool such as that described in U.S. Pat. No. 6,217,573.

Figure 2:
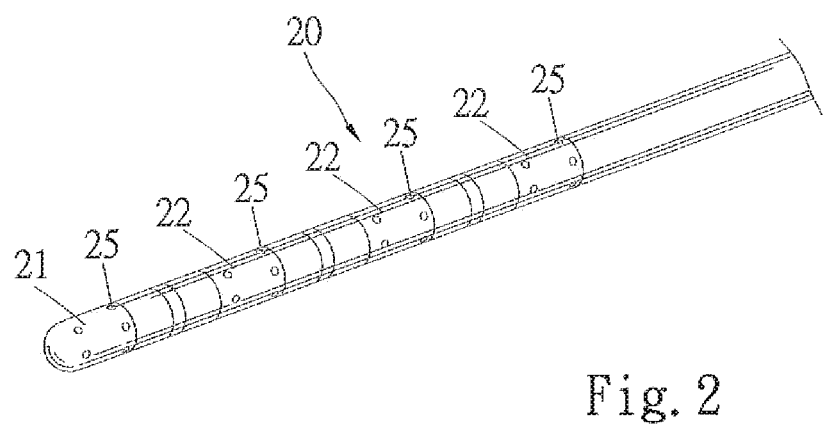
FIG. 2 is a perspective view of the catheter distal region according to an aspect of the inventive subject matter.

In FIG. 2, catheter distal region 20 has bands of electrodes 22 positioned spaced apart in different longitudinal sections. Each band of electrodes 22 has elution holes 25 located in the same longitudinal sections. At the terminal end is catheter tip 21, also having electrodes. Catheter tip 21 can be manufactured separately and attached to the rest of the elongated catheter body.

The contemplated catheter tip 21 can be made of suitable biocompatible materials to conduct RF energy and to withstand temperature extremes. Suitable materials include natural and synthetic polymers, various metals and metal alloys, naturally occurring materials, textile fibers, glass and ceramic materials, sol-gel materials, and all reasonable combinations thereof. In one embodiment, the catheter tip 21 is made of 90% platinum with 10% iridium.

FIG. 3 shows an exemplary embodiment of the catheter tip 21, having a through hole 26 and groove 28. Hole 26 and groove 28 are used to help attaching the catheter tip 21 to the catheter body 18. Catheter body 18 has corresponding structures to matingly couple to the groove 28 and hole 26.

FIG. 4 is a side view of the catheter tip 21. Exemplary embodiments of the catheter tip 21 have two rows of elution holes 25. In this figure, line A-A represents the first row of the elution holes and line B-B represents the second row of elution holes. The terminal end of the tip can be in any configuration, and may be spherical. The distance K1 between the most distal tip of the spherical end to the center of the first row of elution holes preferably may be about 0.039 inches in one embodiment. The distance K2 between edge 29 to the center of the second row of elution holes is may be about 0.020 inches. The diameter of both rows of elution holes are preferably may be about 0.016 inches. As for arrangement of electrodes, mapping devices and sensors, these can be referenced from known ablation catheters such as U.S. Pat. No. 6,611,699.

Figures 4A, 4B:
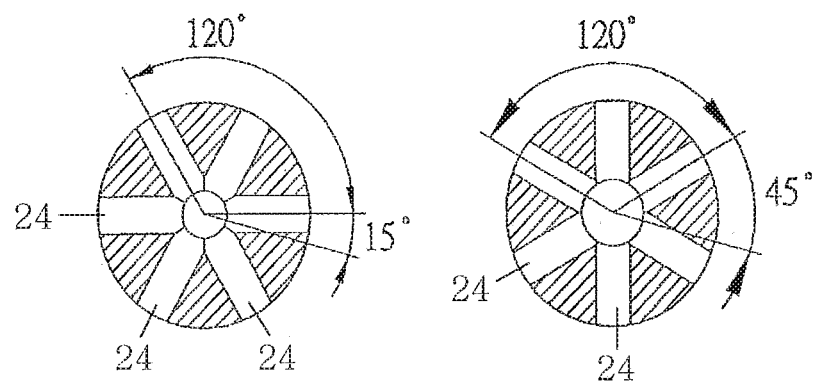
FIG. 4A is a cross sectional view of the catheter tip of FIG. 4 at line A-A, according to an aspect of the inventive subject matter.
FIG. 4B is a cross sectional view of the catheter tip of FIG. 4 at line B-B, according to an aspect of the inventive subject matter.

The number and configuration of elution holes 25 depends on the intended use of the catheter. For example, FIG. 4 shows a configuration where six elution holes 25 are provided in each of the two rows. Each elution hole 25 is fluidly connected with main lumen 23 via ducts 24. Referring to FIGS. 4A and 4B, this configuration provides six ducts 24 radially spread out and spaced evenly from each other in substantially the same degree of angle. This configuration allows all around irrigation and cooling. In comparing FIG. 4A and 4B, the two rows of elution holes are offset by about 15 degrees. By doing so, the offset rows of elution holes provide more evenly distributed irrigation. It is also contemplated that these two rows may be offset by between 15-45 degrees, or more specifically, by about 30 degrees.

Figure 5:
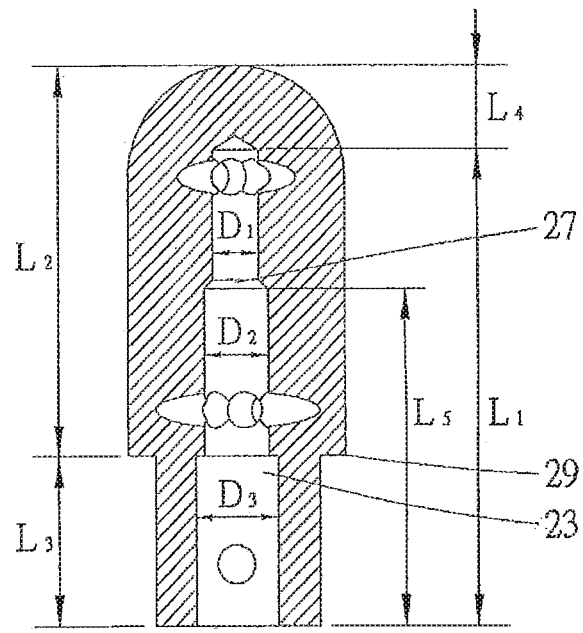
FIG. 5 is a longitudinal cross sectional view of the catheter tip of FIG. 4 at line C-C, according to an aspect of the inventive subject matter.

FIG. 5 provides exemplary dimensions of the various elements in the catheter tip 21. In one embodiment, the diameter D1 of the distal portion of the main lumen may be about 0.019 inches, and the proximal portion of the lumen, after the tapered flow constrictor 27, may have a diameter D2 of about 0.028 inches. The diameter D3 of the main lumen at the neck portion of the catheter tip 21 may be about 0.034 inches. In other embodiments, the diameter of main lumen may range from about 0.005 inches to about 0.045 inches, and the tapered section may decrease the diameter by about 5% to about 40% comparing the two diameters immediately adjacent the tapered section.

The terminal end of the main lumen may end in a flat cone shape, and the distance Li from the edge of the flat cone to the proximal end of the neck portion may be about 0.194 inches. The distance L2 from the tip of the spherical end to the edge 29 may be about 0.158 inches. The distance L3 of the neck from the end of the neck to the edge 29 may be about 0.065 inches. The distance L4 from the edge of the flat cone to the terminal tip of the sphere may be about 0.030 inches. Distance L5 is measured from the larger edge of the tapered flow constrictor 27 to the end of neck, and it is may be about 0.135 inches.

Figure 6:
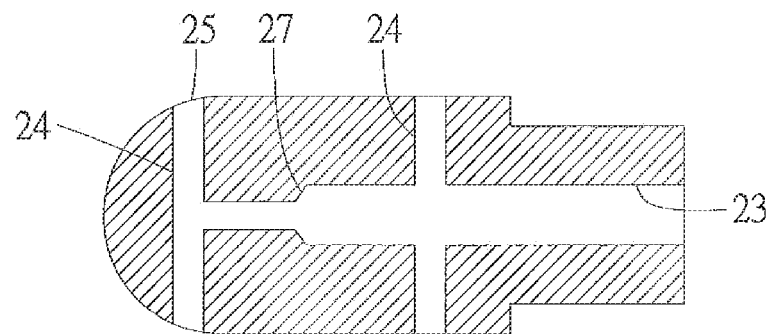
FIG. 6 is a longitudinal cross section view of a catheter tip illustrating varied lumen diameter, according to an aspect of the inventive subject matter.
Figure 7:
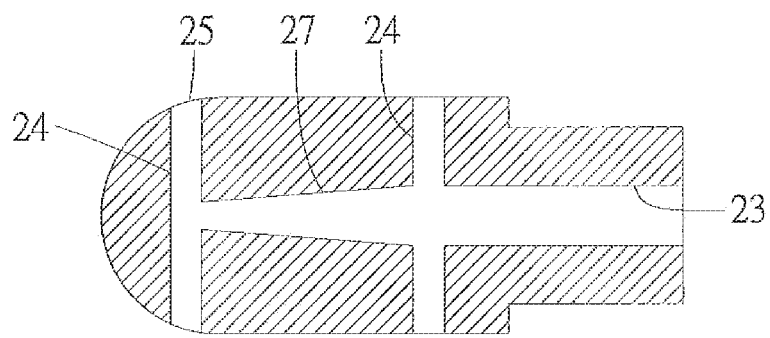
FIG. 7 is a longitudinal cross section view of a catheter tip illustrating varied lumen diameter, according to an aspect of the inventive subject matter.

FIGS. 6 and 7 illustrate different possible configurations of the flow constrictor 27. The flow constrictor 27 limits or constricts the volume of fluid as the fluid passes toward the distal end of the catheter tip. By decreasing the main lumen 23 diameter using a flow constrictor 27 located substantially equidistant from the first row and from the second row, as shown in FIG. 6, the volume of fluid reaching the first row of elution holes 25 is effectively decreased, causing fluid output in the first row of elution holes 25 to be substantially the same volume as the fluid output in the second row. That is, all rows of the elution holes 25 that are disposed along the length of the electrode region may have substantially the same outflow rate. Without a flow constrictor 27, the irrigation system will have an imbalanced outflow pattern where more fluid outflow occurs at the first row. A number of factors are involved in designing an irrigation system with even distribution rate along all of the elution holes. Some of these factors include: size of lumen diameter, percentage differences in diameter decrease, distance between adjacent rows of ducts, diameter of ducts, and tilt angle (if any) of the ducts relative to the main lumen. It is contemplated that the irrigation path described may be modified as dictated by the functional needs of particular applications. For example, in some medical applications more irrigation may be desired in the proximal end and any one or more of the above factors may be adjusted to create an irrigation system to provide more output flow in the proximal region.

In some embodiments, the ducts 24 may have walls with spiral grooves, influencing flow pattern of the fluid flowing through the ducts 24. With such spiral grooves, the fluid comes out of elution holes 24 with an outwardly spraying swirl. This spraying pattern tends to minimize direct impact of the fluid on vessel walls. The spiral grooves can be formed by using an appropriate drill bit. The duct wall can alternatively have other irregular patterns to create other outflow patterns.

In FIG. 7, the flow constrictor 27 is a gradual taper that gradually decreases the main lumen diameter, as opposed to a relatively more abrupt taper seen in FIG. 6. Ether abrupt taper or gradual taper, both are preferred over straight angle drop in diameter, because a straight angle drop in diameter can create undesirable eddy currents in the main lumen.

Figure 8:
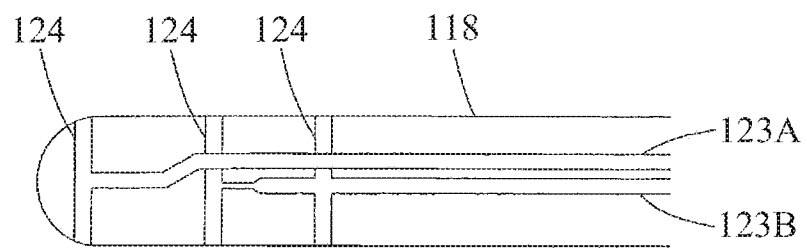
FIG. 8 is a longitudinal cross section view of a catheter distal section illustrating an embodiment having multiple lumens for fluid delivery, according to an aspect of the inventive subject matter.
Figure 9:
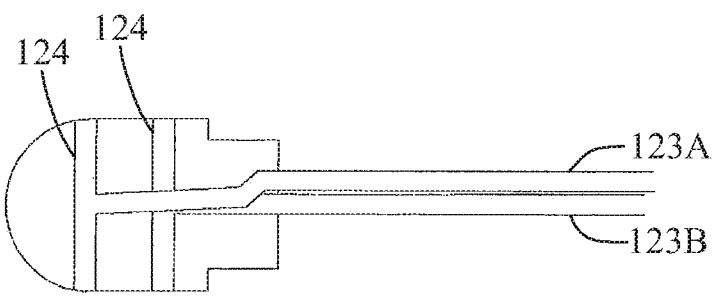
FIG. 9 is a longitudinal cross section view of a catheter distal section illustrating an embodiment having multiple lumens for fluid delivery, according to an aspect of the inventive subject matter.
Figure 10:
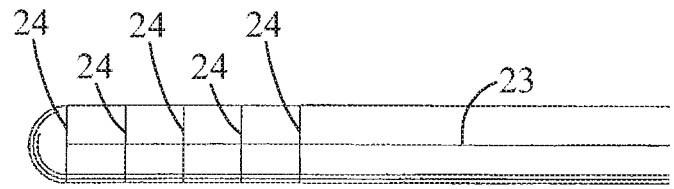
FIG. 10 is a diagrammatic illustration of side channel configuration, according to an aspect of the inventive subject matter.

FIGS. 8, 9, and 10 show yet other embodiments of the present invention. These embodiments have two separate lumens 123A, 123B, with each lumen supplying fluid to corresponding rows of ducts 124. These embodiments are perhaps less desirable because multiple lumens take up precious cross sectional space in catheter body 118. However, it is recognized that even distribution of fluid can be achieved by having separate fluid delivery lumens for separate rows of ducts, with each lumen being precisely pressure and volume flow controlled.

Figure 11:
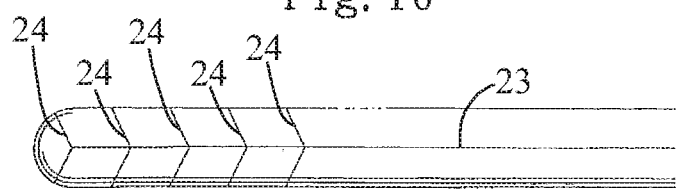
FIG. 11 is a diagrammatic illustration of side channel configuration, according to an aspect of the inventive subject matter.
Figure 12:
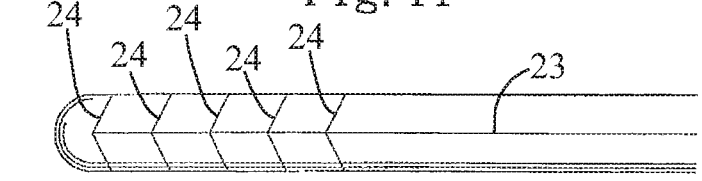
FIG. 12 is a diagrammatic illustration of side channel configuration, according to an aspect of the inventive subject matter.
Figure 13:
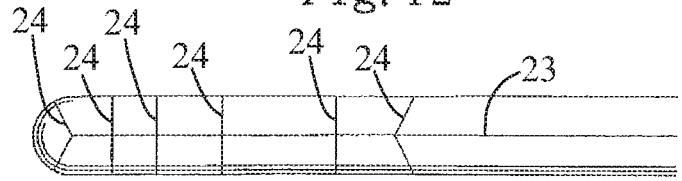
FIG. 13 is a diagrammatic illustration of side channel configuration, according to an aspect of the inventive subject matter.
Figure 14:
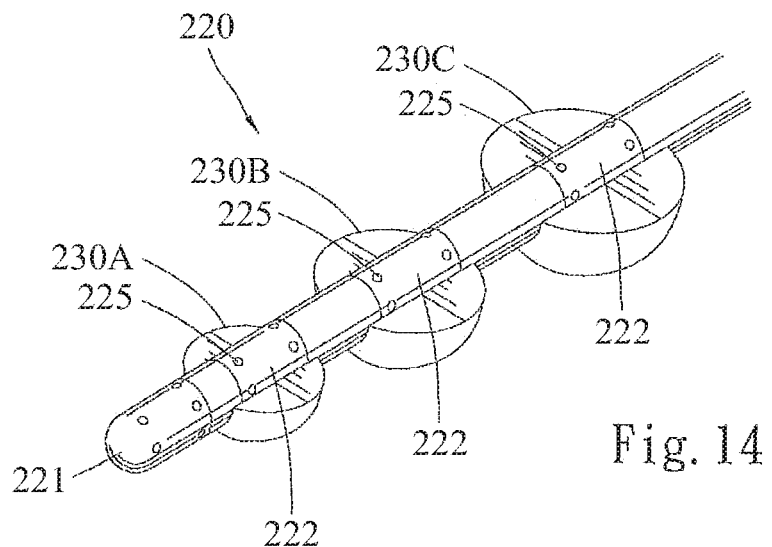
FIG. 14 is a perspective top view of the catheter distal region having inflatable balloons fully inflated, according to an aspect of the inventive subject matter.
Figure 15:
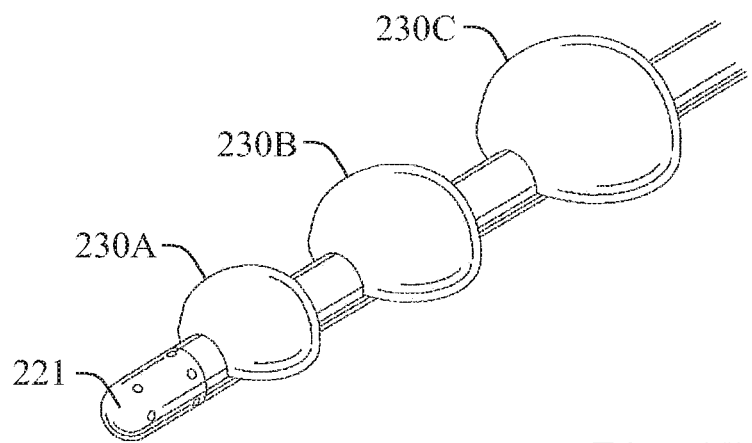
FIG. 15 is a perspective bottom view of the catheter distal region having inflatable balloons fully inflated, according to an aspect of the inventive subject matter.
Figure 16:
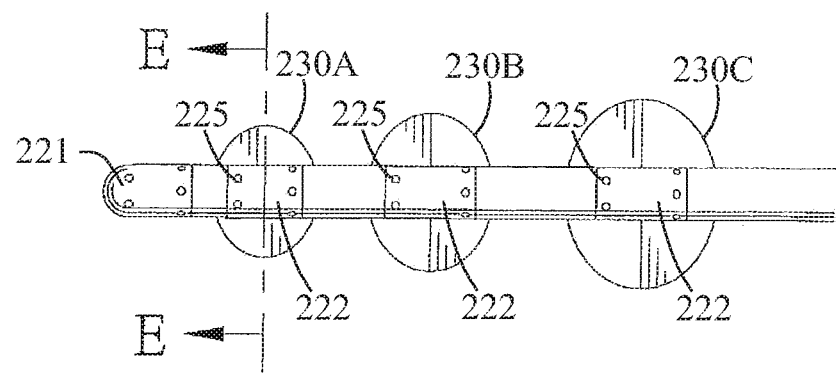
FIG. 16 is a top view of the catheter distal region having inflatable balloons fully inflated, according to an aspect of the inventive subject matter.
Figure 17:
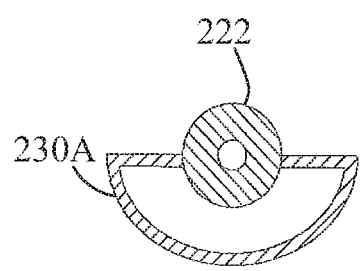
FIG. 17 is a crossectional view of the catheter distal region of FIG. 16 at line E-E, according to an aspect of the inventive subject matter.

As will be illustrated in connection with FIGS. 10-13, the irrigation system can be advantageously enhanced by arranging the angle of the ducts 24 relative to the main lumen 23. A flow constrictor is omitted from these figures but it is contemplated that a flow constrictor may be required depending on the type of flow output desired. An angle between a longitudinal axis of each of the plurality of ducts 24 and the longitudinal axis of the main lumen may be formed, for example, between 35 to 90 degrees, more specifically, between 45 to 90 degrees, and even more specifically between 80 to 90 degrees. In FIG. 10, the ducts 24 are substantially perpendicular to the main lumen 23. In FIG. 11, all of the ducts 24 are tilted towards the distal end, creating a general flow towards the front. In FIG. 12, all of the ducts 24 are tilted towards the proximal end, creating a general flow towards the back. In FIG. 13, a mixture of all three types is provided, creating a general flow away from the ablation area.

In FIG. 14-17, three inflatable balloons 230A, 230B, 230C can be optionally provided to the electrode catheter as discussed above. Alternatively, this can be a balloon catheter with optional electrodes for ablation. The balloons 230 help navigate and position the electrode 222 to the targeted ablation site. As discussed earlier, elution holes 225 may be provided for irrigation purposes, and the catheter has a catheter tip 221. The catheter is first inserted into the patient while the balloon 230 is deflated. Once the user finds the targeted ablation location, the balloon 230 inflates, pushing the electrode side 222 of the catheter region against or closer to the ablation area. As opposed to electrodes described above, these embodiments have electrodes 222 on only the top side of the catheter distal portion. The underside has inflatable balloons 230.

Contemplated devices may have just a single balloon 230, or a plurality of balloons 230. Where a plurality of balloons 230 are provided, the balloons can be of the same size and shape, or alternatively, each balloon 230 can have a distinct shape and size. An exemplary embodiment includes three balloons 230A, 230B, 23 DC, with the smallest one at the distal end, and the largest one on the proximal end. This configuration facilitates manipulation of the catheter in a funnel-shaped vessel. When in a funnel-shaped vessel closely corresponding to shape of the balloon catheter distal region when inflated, the balloon catheter in FIGS. 14-17 can more fittingly secure itself and position the electrode at the ablation region. Exemplary balloons may be half-dome shaped, and may have a cross-sectional shape resembling a half circle. Also contemplated is a configuration having at least one inflatable balloon, where at least one balloon has an inflated shaped that resembles a longitudinally-dissected cone, or half-cone. By providing one balloon, or a plurality of balloons, an overall general shape that may be provided that corresponds to a funnel-shaped vessel. This overall general shape can be a longitudinally dissected cone shape, a longitudinally dissected oval (egg-like) shape where a distal end is smaller than the proximal end, or any other shapes where the cross-sectional area is smaller at the distal portion of the overall shape than at its proximal portion. The device may use typical controlling parts and other related configuration for using and positioning the balloon 230, such as those disclosed in U.S. Pat. Nos. 7,137,395 and 6,780,183.

Balloon catheter devices are well known and general features (e.g. size, shape, materials) of the balloons 230 may be in accordance with conventional balloons. In one embodiment, the balloons 230 is may be made of flexible medical-grade silicone rubber. Alternatively, the balloon 230 may be made of other biocompatible and distendable materials, such as polyethylene terepthalate (PET).

While the various embodiments of the irrigation system is herein disclosed as suitable for ablation catheters that perform tissue ablation, and the fluid being suitable cooling fluid such as saline, the same uniform distribution concept can be applied to drug delivery catheters desiring to delivery therapeutic fluid at a uniform rate among the many delivery bores on the catheter distal region. Thus, specific embodiments and applications of multi-electrode irrigated catheters with balloons have been disclosed. It should be apparent, however, that many more modifications besides those already described are possible without departing from the inventive concepts herein. The inventive subject matter, therefore, is not to be restricted except in the spirit of the appended claims.

What is claimed is:

1. A tip portion for a catheter, the tip portion comprising a first band electrode having a sidewall, a second band electrode having a sidewall, and an internal lumen, each of the first band electrode and the second band electrode comprising a plurality of elution holes extending through the respective sidewalls and being spaced apart from one another along a longitudinal length of the tip portion, the tip portion further comprising a plurality of longitudinally spaced ducts in fluid communication with the lumen, each of the longitudinally spaced ducts extending from the lumen to a respective one of the plurality of elution holes, wherein a diameter of the lumen is varied between at least two of the longitudinally spaced ducts.

2. The tip portion of claim 1, wherein the diameter of the lumen is smaller at a distal end of the tip portion than at a proximal end of the tip portion such that a substantially uniform outflow rate of fluid is produced in substantially all of the plurality of elution holes.

3. The tip portion of claim 1, wherein the plurality of elution holes includes a first row of elution holes and a second row of elution holes, the diameter of the lumen is varied to produce a higher outflow rate of fluid through the first row of elution holes than through the second row of elution holes, wherein the first row of elution holes is closer to a distal end of the tip portion than is the second row of elution holes.

4. The tip portion of claim 1, wherein the plurality of elution holes includes a first row of elution holes and a second row of elution holes, the diameter of the lumen is varied to produce a higher outflow rate of fluid through the second row of elution holes than through the first row of elution holes, wherein the second row of elution holes is farther from a distal end of the tip portion than is the first row of elution holes.

5. The tip portion of claim 1, wherein the diameter of the lumen is varied to produce an overall uniform outflow rate through the plurality of elution holes except at a predetermined location, wherein at least one elution hole at the predetermined location has a first outflow rate that is different from the uniform outflow rate.

6. The tip portion of claim 1, wherein the diameter of the lumen decreases in a distal direction between the at least two of the longitudinally spaced ducts.

7. The tip portion of claim 1, wherein the diameter of the lumen decreases in a distal direction between the first band electrode and the second band electrode.

8. An irrigated catheter comprising:
a catheter body comprising a distal region including a terminal end, a longitudinal axis, a first band electrode, and a second band electrode, each of the first band electrode and the second band electrode comprising a sidewall; and
an irrigation path extending through the distal region, the irrigation path comprising:
a fluid delivery lumen extending along the longitudinal axis; and
a first plurality of elution holes extending through the first band electrode sidewall and a second plurality of elution holes extending through the second band electrode sidewall, each elution hole of the first plurality of elution holes and the second plurality of elution holes in fluid communication with the fluid delivery lumen, wherein a diameter of the fluid delivery lumen is varied between a first elution hole of the first plurality of elution holes and a second elution hole of the second plurality of elution holes.

9. The irrigated catheter of claim 8, wherein the first plurality of elution holes includes a first row of elution holes and a second row of elution holes, the first row of elution holes spaced from the second row of elution holes along the longitudinal axis.

10. The irrigated catheter of claim 8, wherein the diameter of the lumen decreases in a distal direction between the first plurality of elution holes and the second plurality of elution holes.

11. The irrigated catheter of claim 8, wherein the diameter of the lumen is smaller at the terminal end than at a location proximal to the terminal end such that a substantially uniform outflow rate of fluid is produced in the first and second pluralities of elution holes.

12. The irrigated catheter of claim 8, further comprising a tip electrode at the terminal end, the tip electrode comprising a third plurality of elution holes extending therethrough.

13. The irrigated catheter of claim 8, further comprising a plurality of ducts in fluid communication with the lumen, wherein each elution hole of the first plurality of elution holes and the second plurality of elution holes is in fluid communication with a respective one of the ducts of the plurality of ducts.

14. The irrigated catheter of claim 8, wherein the diameter of the lumen is varied between the first band electrode and the second band electrode.

15. The irrigated catheter of claim 8, wherein the first and second band electrodes are configured to contact tissue and deliver energy to the tissue.

16. An irrigated catheter comprising:
a catheter body including a first band electrode, a second band electrode and a lumen, each of the band electrodes including a sidewall, the catheter body defining a longitudinal axis; and
a first plurality of elution holes extending through the first band electrode sidewall and in fluid communication with the lumen, and a second plurality of elution holes extending through the second band electrode sidewall and in fluid communication with the lumen, wherein a diameter of the lumen is varied between a first elution hole of the first plurality of elution holes and a second elution hole of the second plurality of elution holes.

17. The irrigated catheter of claim 16, wherein the catheter body further comprises a tip electrode including a third plurality of elution holes that are in fluid communication with the lumen.

18. The irrigated catheter of claim 16, wherein the first and second band electrodes are configured to contact tissue and deliver energy to the tissue.

19. The irrigated catheter of claim 16, wherein the diameter of the lumen decreases between the first band electrode and the second band electrode.

20. The irrigated catheter of claim 16, wherein the diameter of the lumen decreases between the first elution hole and the second elution hole.

* * * * *